(12) United States Patent
El Amm

(10) Patent No.: US 12,048,459 B2
(45) Date of Patent: Jul. 30, 2024

(54) DISTRACTION OSTEOGENESIS DEVICE AND METHODS

(71) Applicant: THE BOARD OF REGENTS OF THE UNIVERSITY OF OKLAHOMA, Norman, OK (US)

(72) Inventor: Christian A. El Amm, Oklahoma City, OK (US)

(73) Assignee: THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 0 days.

(21) Appl. No.: 17/735,295

(22) Filed: May 3, 2022

(65) Prior Publication Data
US 2022/0346839 A1 Nov. 3, 2022

Related U.S. Application Data

(60) Provisional application No. 63/183,406, filed on May 3, 2021.

(51) Int. Cl.
*A61B 17/66* (2006.01)
*A61B 17/80* (2006.01)

(52) U.S. Cl.
CPC .......... *A61B 17/66* (2013.01); *A61B 17/8009* (2013.01)

(58) Field of Classification Search
CPC ..... A61B 17/66; A61B 17/663; A61B 17/666; A61B 17/688; A61B 17/7055; A61B 17/8023; A61B 17/8009
See application file for complete search history.

(56) References Cited

U.S. PATENT DOCUMENTS

| 5,700,263 | A | * | 12/1997 | Schendel | A61B 17/663 606/57 |
| 5,885,283 | A | * | 3/1999 | Gittleman | A61B 17/6433 606/904 |
| 5,993,448 | A | * | 11/1999 | Remmler | A61B 17/68 606/53 |

(Continued)

OTHER PUBLICATIONS

Andrade N, Gandhewar T, Kalra R. Development and evolution of distraction devices: Use of indigenous appliances for Distraction Osteogenesis—An overview. Ann Maxillofac Surg. Jan. 2011:1(1):58-65.

(Continued)

*Primary Examiner* — Matthew J Lawson
(74) *Attorney, Agent, or Firm* — Parker Highlander PLLC

(57) ABSTRACT

The present disclosure is directed to implantable distraction osteogenesis devices and methods of their use. In a non-limiting embodiment, the device has a guide, a first bone attachment device slidably engaged with the guide, a force delivery mechanism coupled to the first bone attachment device and operably engaged with the guide, a regulator operably engaged with the force delivery mechanism, and a second bone attachment device rigidly fixed to the guide, wherein the force delivery mechanism is configured to exert a force to move the first bone attachment device along the guide at a predetermined rate, and the regulator is configured to control the movement of the first bone attachment device along the guide without percutaneous intervention.

17 Claims, 8 Drawing Sheets

(56) References Cited

U.S. PATENT DOCUMENTS

| | | | | |
|---|---|---|---|---|
| 6,113,599 | A * | 9/2000 | Landsberger | A61B 17/663 606/57 |
| 8,177,789 | B2 * | 5/2012 | Magill | A61B 17/663 606/105 |
| 2006/0235424 | A1 * | 10/2006 | Vitale | A61B 17/7216 606/90 |
| 2009/0088766 | A1 * | 4/2009 | Magill | A61B 17/663 606/280 |
| 2009/0192514 | A1 * | 7/2009 | Feinberg | A61B 17/8004 606/90 |
| 2013/0138017 | A1 * | 5/2013 | Jundt | A61B 17/66 601/2 |
| 2014/0324046 | A1 | 10/2014 | Vicatos et al. | |
| 2019/0209211 | A1 * | 7/2019 | Charest | A61B 17/7016 |
| 2019/0388122 | A1 | 12/2019 | Taylor et al. | |
| 2021/0393301 | A1 | 12/2021 | Forsell | |

OTHER PUBLICATIONS

Brody-Camp S, Winters R. Craniofacial Distraction Osteogenesis. Dec. 29, 2021. In: StatPearls [Internet]. Treasure Island (FL): StatPearls Publishing; Jan. 2022.

Hatefi S, Etemadi Sh M, Yihun Y, Mansouri R, Akhlaghi A. Continuous distraction osteogenesis device with MAAC controller for mandibular reconstruction applications. Biomed Eng Online. Apr. 8, 2019;18(1):43.

Hatefi S, Hatefi K, Le Roux F, Alizargar J, Behdadipour Z, Yihun Y, Abou-El-Hossein K. Review of automatic continuous distraction osteogenesis devices for mandibular reconstruction applications. Biomed Eng Online. Apr. 1, 2020;19(1):17.

Chung et al., "An Implantable Battery System for a Continuous Automatic Distraction Device for Mandibular Distraction Osteogenesis", Journal of Medical Devices, 4:045005-1, 2010.

* cited by examiner

DISTRACTION OSTEOGENESIS DEVICE AND METHODS

CROSS-REFERENCE TO RELATED APPLICATIONS

This application claims priority to U.S. Provisional Patent Application Ser. No. 63/183,406 filed May 3, 2021, the entire contents of which are incorporated herein by reference.

BACKGROUND

Distraction osteogenesis (DO) devices are commonly used in a wide variety of medical procedures for reconstruction or repair of malformed and under-developed bones, bone surgically removed for cancer, or bones lost to trauma. The bone adjustment is imparted slowly over a long period of time. The target bones could be long bones of limbs, fingers, or flat bones of the head and face. It has also been applied in some cases to bones of the trunk. DO is less invasive and less likely to cause infection than alternatives such as bone graft. It also has the advantage of progressive stretching of the soft tissues around the bone, leading to less relapse.

The process comprises initially surgically separating the bone in two (or more) pieces, and then gradually moving the pieces apart into a final position. The interface between the two bones initially fills with "healing bone", or "callus," and the distraction process occurs at a graduated and precise rate, generally 1 mm per 24-hour period, depending on type of bone and age of patient. The rate of separation is critical for success; going too fast will result in replacement of callus with scar tissue in the interface, and going too slow can result in early healing, or "ossification" of the bone gap, and failure of subsequent progression.

Devices include at least a first part for attachment to the first bone including commonly-threaded pins or plate-and-screws, a second part comprising the same for the second bone, and a trajectory guide mechanism to separate the parts at a graduated rate, while maintaining the stability of the construct. Commonly, the trajectory guide mechanism comprises a threaded rod with a guiding screw, a rack-and-pinion system, or a piston system. Typically, current systems include a percutaneous external attachment to a drive system, either a handheld screwdriver, or an automated motor or pump to provide the driving force and pace. Some devices have trajectory guides implanted subcutaneously, and are referred to as "internal devices," while others have the trajectory guide outside the skin, and are referred to as "external devices." Both "internal" and "external" devices rely on a communication through the skin to the exterior drive mechanisms. This is due to difficulties with designing implantable drive mechanisms with sufficient torque and control. This communication through the skin, between internal portions and external portions of the system is a significant limitation of the technique, causing frequent contamination with bacteria, possible infections, difficulties with wound care, and pain and distress to the patient and caretakers. Another limitation of the technique is the need for the caretaker to follow specific instructions, such as attaching and turning the screwdriver in a certain direction once or twice a day, which raises potential compliance concerns. Devices and methods which could eliminate or mitigate some or all of these problems would be of great benefit.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The figures are not necessarily to scale and certain features and certain views of the figures may be shown as exaggerated in scale or in schematic in the interest of clarity and conciseness.

5A: Osteosynthesis screw
5B: Footplate body.
5C: External Spring force delivery attachment.

Figure 6:
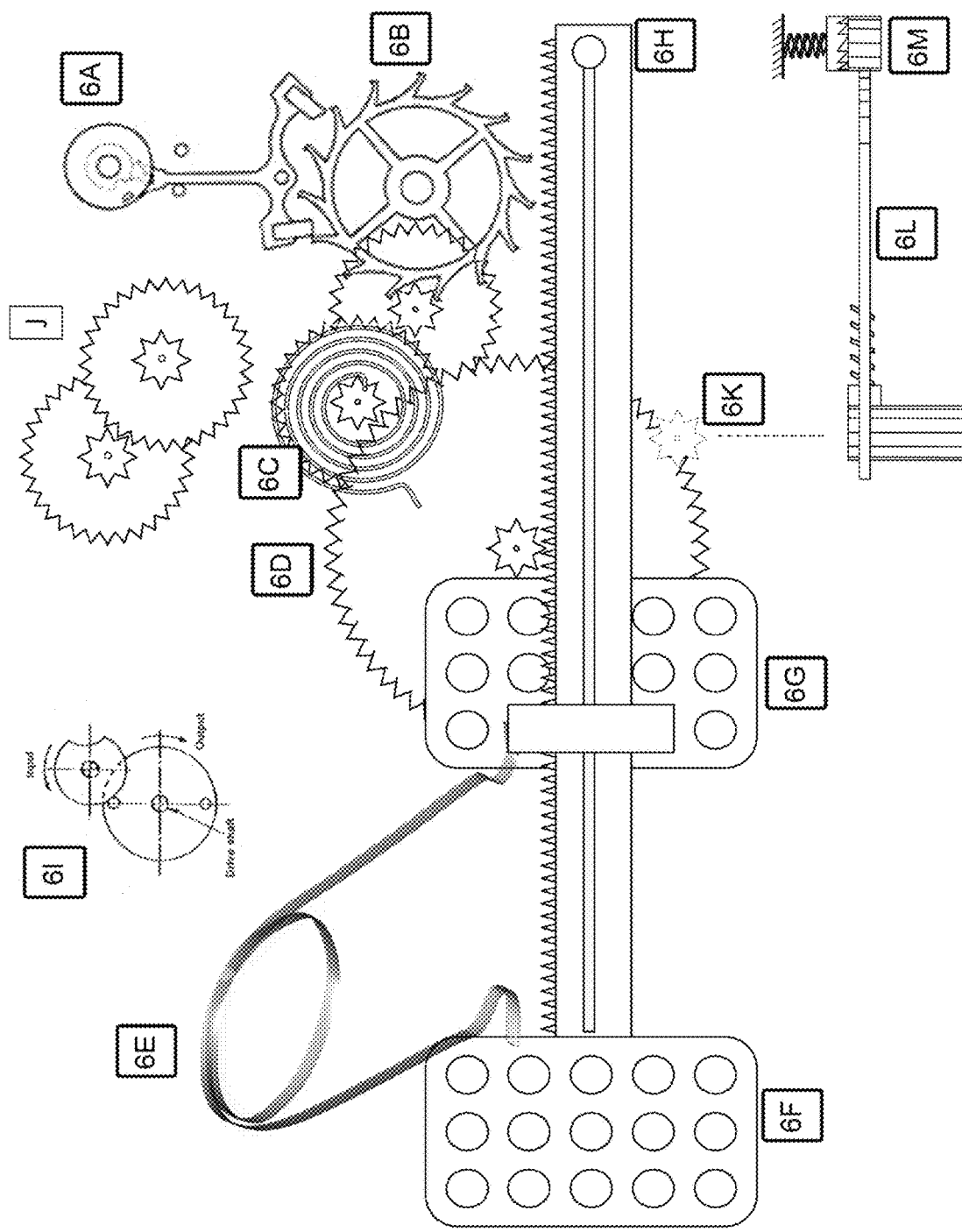

FIG. 6 illustrates a schematic view of an exemplary embodiment of an implantable distraction osteogenesis device according to the present disclosure for high torque applications. The regulator mechanism comprises a timekeeping portion (6A, 6B and 6C) activating a separate striking wheel, which activates a separate gapless escapement mechanism directly on the trajectory guide. Distraction forces are provided by the external springs, which are decoupled from the timing mechanism mainspring. The movement in gear 6D, which in this configuration is known as a scape wheel, is allowed to escape by the input cam shown in 6I. The escape cam is engaged to the timing mechanism "going barrel" mainspring gear 6C with reduction wheel gearing 6J. As used herein, a "going barrel" includes a mainspring barrel (e.g., in a mechanism similar to a watch or clock) that has teeth on its periphery for driving the train and that is mounted on an arbor. Gear 6D in this embodiment is used to wound the "going barrel" mainspring (6C) through a separate ratcheted gearing 6K. In this embodiment, gear 6K engages with arc-gear 6L, that engages with ratcheted gear 6M, connected to the arbor of mainspring 6C, thus reloading the mainspring periodically.

Figure 7:
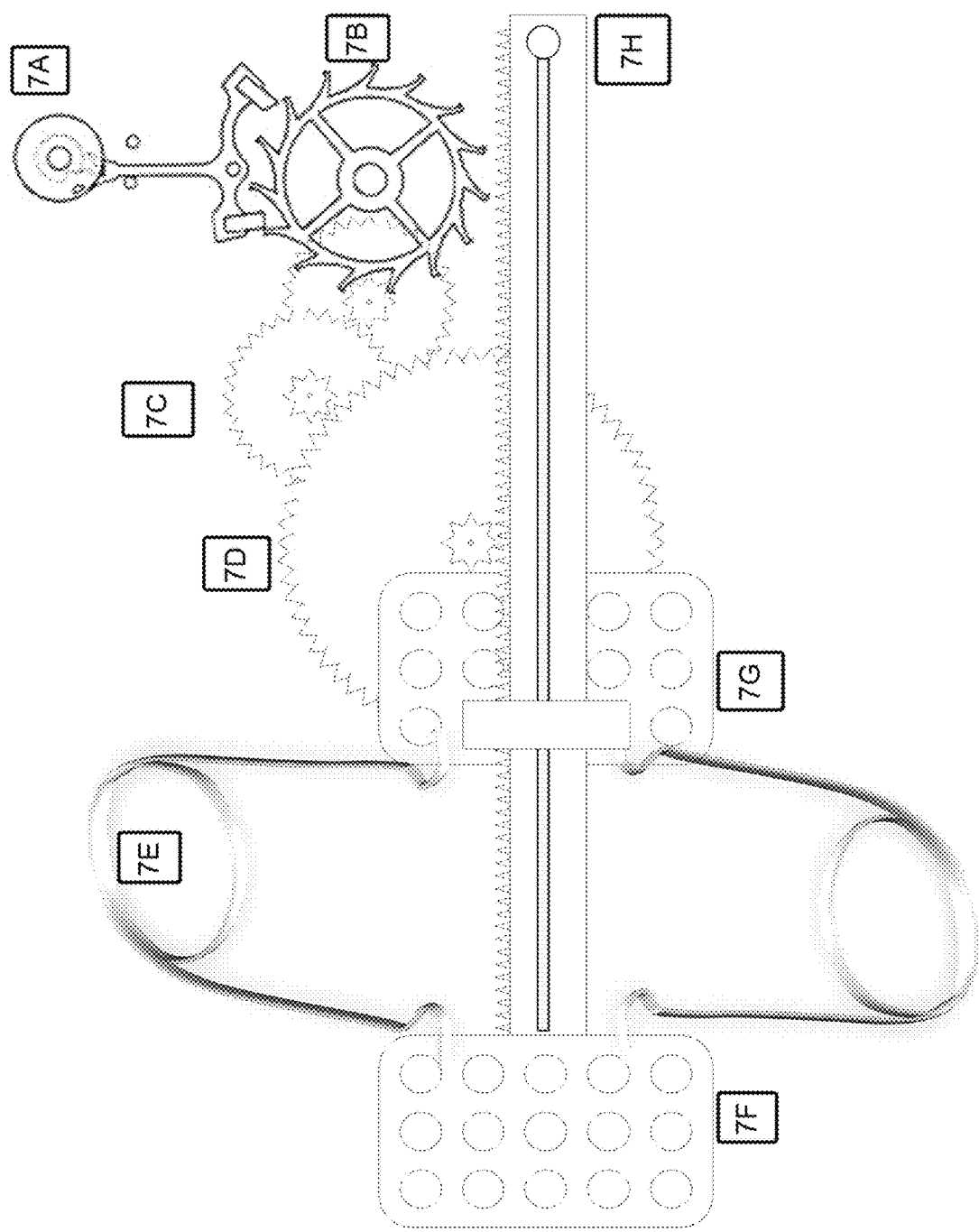

FIG. 7 illustrates a schematic view of an exemplary embodiment of an implantable distraction osteogenesis device according to the present disclosure for a tailored force application with use of two cranial springs with the rest of the device, providing approximately 24 joules of force. In this embodiment, reference numbers and component descriptions are provided as follows:

7A: Balance Wheel and Balance Spring
7B: Escapement Wheel and Lever
7C: Reduction gears
7D: Spiral Spring (Mainspring), Main Wheel, and pinion gear.
7E: Omega cranial spring engaging with footplates to provide additional tailored force
7F: Distal footplate rigidly attached to Trajectory Guide
7G: Proximal footplate with sliding interface with Trajectory Guide and rigid attachment to Regulator mechanism (7A-7D) housing.
7H: Trajectory guide with slotted rack, interfacing with main wheel pinion gear (7D), and end-of-trajectory "stop" attachment.

Figure 8:
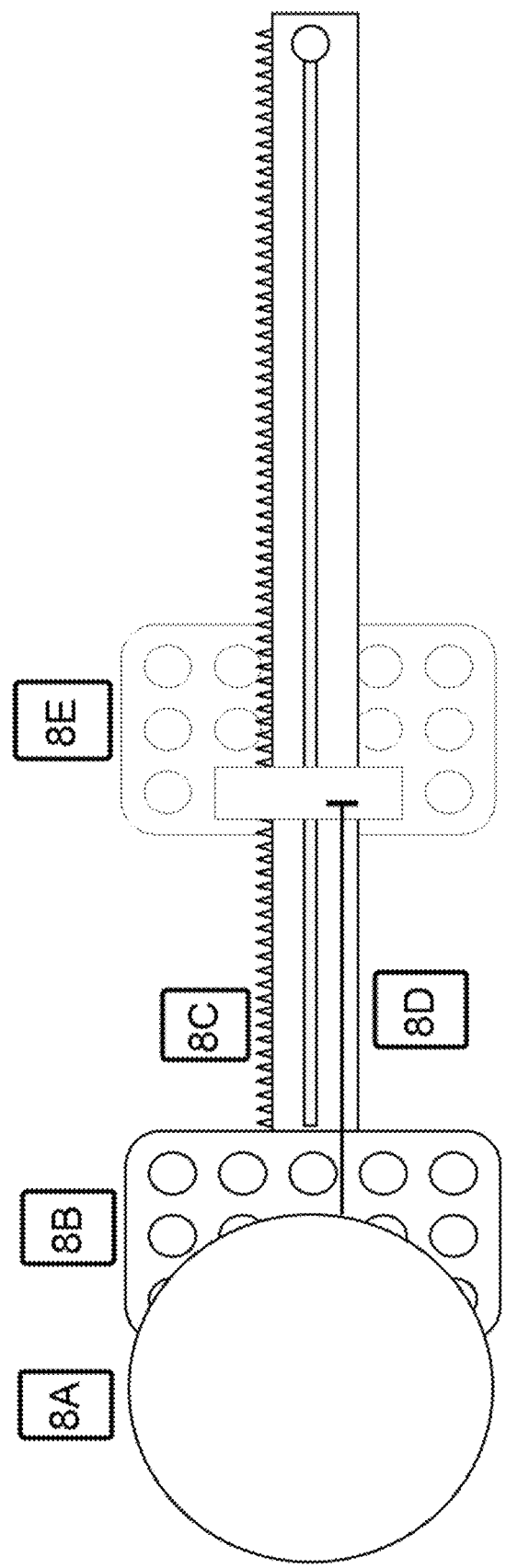

FIG. 8 illustrates an embodiment, wherein the regulator device 8A is attached to distal attachment device 8B, while the trajectory guide comprises part 8C for spatial directional control, and flexible stainless steel wire 8D, which unspools out of the regulator system for control of length of distraction. Flexible wire 8D attaches to proximal attachment device 8E.

DETAILED DESCRIPTION

This disclosure relates to apparatus and methods for distraction osteogenesis. More particularly, this disclosure relates to distraction osteogenesis devices and methods that do not require percutaneous intervention. The present disclosure is directed to a totally subcutaneously implantable device for imparting distraction osteogenesis between two or more osseous segments of a bone, such as a portion of a cranium, a mandible, a facial bone, a femur, a tibia, a fibula, a humerus, an ulna, a radius, a phalange, a metacarpal, a vertebra, or any other type of bone which can befit from expansion or lengthening. The device includes a system to control the path of the movement, a system to regulate the pace of movement, and a system to provide and adjust the forces applied to separate the osseous segments. Since the device is completely subcutaneously implantable, the system eliminates the need for a percutaneous attachment for externally manipulating the internal portion of the device.

In one exemplary, non-limiting, embodiment, the device is an implantable distraction osteogenesis device comprising a guide, a first bone attachment device slidably engaged with the guide, a force delivery mechanism coupled to the first bone attachment device and operably engaged with the guide, a regulator operably engaged with the force delivery mechanism, and a second bone attachment device rigidly fixed to the guide, wherein the force delivery mechanism is configured to exert a force to move the first bone attachment device along the guide at a predetermined rate; and the regulator is configured to control the force delivered to the first bone attachment device by the force delivery mechanism thereby controlling movement of the first bone attachment device along the guide without percutaneous intervention. In a non-limiting embodiment, the regulator may be configured to control movement of the first bone attachment device along the guide at a rate of 0.1 millimeter (mm) to 2 mm per 24 hours.

Before further describing various embodiments of the present disclosure in more detail by way of exemplary description, examples, and results, it is to be understood that the embodiments of the present disclosure are not limited in structure and application to the details as set forth in the following description. The embodiments of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the present disclosure has been described in terms of particular embodiments, it will be apparent to those of skill in the art that variations may be applied to the apparatus and/or methods and in the steps or in the sequence of steps of the methods described herein without departing from the spirit and scope of the inventive concepts as described herein. Any methods, devices and materials similar or equivalent to those described herein can be used in the practice or testing of the embodiments of the present disclosure. All such similar substitutes and modifications apparent to those having ordinary skill in the art are deemed to be within the spirit and scope of the inventive concepts as disclosed herein. The inclusion of any particular embodiment, feature or function within the Abstract is not intended to limit the scope of the present disclosure to such embodiment, feature or function. Titles and headings of sections of this disclosure are for convenience only and shall not affect the scope or interpretation of any aspect of this disclosure.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the apparatus, methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the terms "at least one" or "plurality" will be understood to include one as well as any quantity more than one, including but not limited to, 2, 3, 4, 5, 6, 7, 8, 9, 10, 15, 20, 30, 40, 50, 100, or any integer inclusive therein, and/or any range described herein. The terms "at least one" or "plurality" may extend up to 100 or 1000 or more, depending on the term to which it is attached; in addition, the quantities of 100/1000 are not to be considered limiting, as higher limits may also produce satisfactory results. In addition, the use of the term "at least one of x, y and z" (or any similar combination of terms) will be understood to include x alone, y alone, and z alone, as well as any combination of x, y and z, such as x and y, x and z, y and z, and x, y, and z.

Where the specification or claims refer to "an additional" element, that does not preclude there being more than one of the additional element. That is, where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Any embodiment of any of the present apparatus, methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The term "or combinations thereof" as used herein refers to all permutations and combinations of the listed items preceding the term. For example, "a, b, c, or combinations thereof" is intended to include at least one of: a, b, c, ab, ac, bc, or abc, and if order is important in a particular context, also ba, ca, cb, cba, bca, acb, bac, or cab. Continuing with this example, expressly included are combinations that contain repeats of one or more item or term, such as bb, aaa, aab, bbc, aaabcccc, cbbaaa, cababb, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the apparatus or composition, the method used to administer the apparatus or composition, or the variation that exists among the components, objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximately", where used herein when referring to a measurable value of a dimension, quantity, or characteristic such as an amount, a temporal duration, thickness, width, length, density, and the like, is meant to encompass, for example, variations of ±20% or ±10%, or ±5%, or ±1%, or ±0.1% from the specified value, as such variations are appropriate to construct the apparatus or perform the disclosed methods and as understood by persons having ordinary skill in the art. As used herein, the term "substantially" means that the subsequently described event or circumstance completely occurs or that the subsequently described feature, event, or circumstance occurs to a great extent or degree. For example, the term "substantially" means that the subsequently described event or circumstance occurs at least 75% of the time, at least 80% of the time, at least 90% of the time, at least 95% of the time, or at least 98% of the time.

As used herein any reference to "one embodiment," "an embodiment," "some embodiments," "particular embodiment," or "a specific embodiment" or similar terminology means that a particular element, feature, structure, or characteristic described in connection with the embodiment is included in at least one embodiment. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the inventive concepts disclosed herein. Whether specifically noted as non-limiting examples or not, language describing examples, including "such as", "including", "other instances", "merely exemplary", "for instance", "for example", "etc.", e.g.", "as well as", "the like", and similar terms are understood to be non-limiting.

Variations of components and/or parameters discussed in relation to one embodiment described herein can be incorporated into other embodiments described herein. In non-limiting examples, ranges and related gradations for different temperatures, pressures, time, number of cycles, ratios, volumes, dimensions, current, voltage, fluorescence, brightness, and/or distances discussed in relation to one embodiment can also be incorporated into other embodiments disclosed herein. Additionally, in non-limiting embodiments, different configurations of components, including non-limiting examples such as pistons, chambers, cylinders, probes, sensors, power sources, detectors, lysis, and/or reagents discussed in relation to one embodiment can also be incorporated into other embodiments disclosed herein.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-30 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, as well as sub-ranges within the greater range, e.g., for 1-30, sub-ranges include but are not limited to 1-10, 2-15, 2-25, 3-30, 10-20, and 20-30. Reference to a range of 1-90 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and 90, as well as sub-ranges within the greater range, e.g., for 1-60, sub-ranges include but are not limited to 1-50, 2-50, 5-60, 5-45, 10-60, 10-40, 15-30, 1-85, 10-85, 20 to 5-70, 10-70, 28-70, and 14-56. Reference to a series of ranges includes ranges which combine the values of the boundaries of different ranges within the series. Thus, to illustrate reference to a series of ranges, for example, a range of 1-1,000 includes, but is not limited to, 1-10, 2-15, 2-25, 3-30, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 1 mm to 10 m therefore refers to and includes all values or ranges of values, and fractions of the values and integers within said range, including for example, but not limited to, 5 mm to 9 m, 10 mm to 5 m, 10 mm to 7.5 m, 7.5 mm to 8 m, 20 mm to 6 m, 15 mm to 1 m, 31 mm to 800 cm, 50 mm to 500 mm, 4 mm to 2.8 m, and 10 cm to 150 cm. Any two values within the range of 1 mm to 10 m therefore can be used to set lower and upper boundaries of a range in accordance with the embodiments of the present disclosure.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

As used herein, "opposite" is used to indicate in a direction on average that is different to, orthogonal to, or opposing the general net vector of the first direction.

As used herein, when referring to movement of, or action on, a fluid, it is understood that this includes movement of, or action on, a fraction or subset of the fluid.

As used herein, the term "force delivery mechanism" refers to a mechanism which is able to exert a mechanical force on another object and includes but is not limited to springs, motors and hydraulic pistons. Exemplary springs include but are not limited to spiral springs, coil springs, clock spring, mainsprings, omega springs, U-shaped springs, torsion springs, and extension springs. Exemplary motors include electric motors such as but not limited to DC motors, battery-powered motors, piezoelectric motors, stepper motors, and servo motors. In a non-limiting embodiment, an electric motor such as shown in U.S. Patent Application Publication No. 2009/0192514 may be used.

As used herein, the term "percutaneous" means "through the skin" and refers to a procedure or application which occurs by physical passage through the skin such as via needle injection or transcutaneous passage of a drug (e.g., via iontophoresis), or through a port in the skin via which an action takes place (such as manipulation with a tool), but is not intended to include application of wireless transmissions, for example for transmitting radiowaves through the skin to the distraction osteogenesis device of the present disclosure for directing its internal action, altering programming, or powering up an internally-disposed battery. As used herein, the term "subcutaneous" or "subcutaneously" means underneath or below the skin.

The terms "subject" and "patient" are used interchangeably herein and will be understood to refer, in certain embodiments, to a warm-blooded animal, particularly a mammal. Non-limiting examples of animals within the scope and meaning of this term include dogs, cats, rabbits, rats, mice, guinea pigs, chinchillas, horses, goats, cattle, sheep, camelids such as llamas and alpacas, zoo animals, Old and New World monkeys, non-human primates, and humans. Therefore, for example, although the described embodiments illustrate use of the present devices and methods on humans, those of skill in the art would readily recognize that these devices and methods could also be applied to veterinary medicine as well as on other animals described herein.

"Treatment" refers to treatment of a condition, and may include prophylactic or preventative treatment measures for reducing the onset of the condition. The term "treating" refers to applying the presently disclosed apparatus to a subject for treatment of the condition.

As used herein any reference to "we" as a pronoun herein refers generally to laboratory personnel or other contributors who assisted in the laboratory procedures and data collection and is not intended to represent an inventorship role by said laboratory personnel or other contributors in any subject matter disclosed herein.

The inventive concepts of the present disclosure will be more readily understood by reference to the following examples and embodiments, which are included merely for purposes of illustration of certain aspects and embodiments thereof, and are not intended to be limitations of the disclosure in any way whatsoever. Those skilled in the art will promptly recognize appropriate variations of the apparatus, compositions, components, procedures and method shown below.

In particular embodiments, the regulator of the distraction osteogenesis device comprises a balance wheel and balance spring; an escapement wheel and lever; one or more reduction gears; a spiral spring; a primary gear; and a pinion gear. In some embodiments the guide comprises a plurality of teeth, and the pinion gear engages the plurality of teeth. In specific embodiments the spiral spring of the regulator is the force delivery mechanism. The distraction osteogenesis device may include a second force delivery mechanism which may be a spring. In particular embodiments the second force delivery mechanism is an omega spring. In some embodiments the second force delivery mechanism engages both the first attachment device and the second attachment device. In specific embodiments the guide is configured to move the first attachment device in a linear path, and in certain embodiments the guide is configured to move the first attachment device in a pre-defined three-dimensional path.

In particular embodiments the regulator is configured to control movement of the first attachment device along the guide without percutaneous intervention over a period of 1 to 90 days or more (e.g., 1-30 days, 1-42 days, 1-60 days, 1-70 days, or 1-84 days, or any range of days between 1 and 90, more more). In some embodiments the guide has a maximum dimension of 5 centimeters (cm) or less (e.g., 1, 2, 3, 4 or 5 cm), and the regulator has a maximum dimension of 4 cm (e.g., 1, 2, 3 or 4 cm) or less. In specific embodiments the regulator comprises a centrifugal regulator. In certain embodiments the force delivery mechanism is configured to generate a force greater than or equal to 40 Newtons (N) and less than or equal to 70 N (i.e., in a range of about 40 N to about 70 N). In particular embodiments the guide, the first attachment device and the second attachment device are formed from any suitable biocompatible structural material such as metals, including medical grade stainless steel, medical grade titanium, and metal alloys, and plastics and polymers. In some embodiments the guide engages the regulator via a rack-and-pinion gear, an angled gear, an infinite screw, or a spool. In specific embodiments the guide has a stop attachment configured to limit movement of the first attachment device.

Exemplary embodiments of the present disclosure also include a method of causing distraction osteogenesis in a bone of a subject in need of such therapy, including the steps of providing a distraction osteogenesis device as described elsewhere herein; securing the first bone attachment device and the second bone attachment device to the bone of the subject, wherein the distraction osteogenesis device is completely subcutaneously implanted; and actuating the distraction osteogenesis device thereby causing a distraction force to be applied between the first bone attachment device and the second bone attachment device, wherein the distraction osteogenesis device operates without percutaneous intervention after actuation. The distraction osteogenesis device is then operated for a period of time sufficient to enable a predetermined amount of distraction osteogenesis in the bone.

In certain non-limiting embodiments of the method the regulator is configured to control movement of the first attachment device along the guide at a rate of about 0.1 to 2.0 millimeters (mm) per 24 hours, such as 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm per 24 hours. In particular embodiments of the method, the regulator comprises: a balance wheel and balance spring; an escapement wheel and lever; one or more reduction gears; a spiral spring; a primary gear; and a pinion gear. In specific embodiments of the method, the guide comprises a plurality of teeth, and the pinion gear engages the plurality of teeth. In some embodiments of the method, the spiral spring of the regulator applies the distraction force. In certain embodiments of the method, the implantable distraction osteogenesis apparatus comprises a second force delivery mechanism to apply the distraction force. In particular embodiments of the method the second force delivery mechanism is one additional spring. In some embodiments of the method the second force delivery mechanism comprises two or more additional springs. The springs may be omega springs or other springs described herein. Generally the second force delivery mechanism engages the first attachment device and the second attachment device for providing an expansion force therebetween. In specific embodiments of the method the guide is configured to move the first attachment device in a linear path. In certain embodiments of the method the guide is configured to move the first attachment device in a pre-defined three-dimensional path. Particular embodiments of the method further comprise controlling movement of the first attachment device along the guide without percutaneous intervention for a period of at least 30, 60 or 90 days (or other durations described elsewhere herein). In some embodiments of the method the guide has a maximum dimension of 5 cm or less (e.g., 1-5 cm or 2-5 cm), and the regulator has a maximum dimension of 4 cm (e.g., 1-4 cm or 2-4 cm) or less. In specific embodiments of the method the regulator comprises a centrifugal regulator. In certain embodiments of the method the distraction force is in a range of from about 40 N to about 70 N. In particular embodiments of the method, the guide, the first attachment device and the second attachment device are formed from medical grade stainless steel, medical grade titanium, or any other suitable pharmaceutically acceptable metal or metal alloy, or plastic or polymeric material. In some embodiments of the method, the guide engages the regulator via a rack-and-pinion gear, an angled gear, an infinite screw, and/or a spool. In specific embodiments of the method, the guide has a stop attachment configured to limit movement of the first attachment device.

As noted elsewhere herein, in exemplary embodiments the distraction osteogenesis device comprises a guide to control the trajectory of movement of certain components of the device as well as the desired trajectory of bone movement. In certain embodiments, the guide may comprise a deformable slotted rack that can be molded to the desired trajectory of the bone movement (for example convex longitudinally to follow the curvature of a cranium), and still retain sufficient stiffness to guide the trajectory of the distraction process through a pre-defined three-dimensional configuration. Other configurations of the system can include a threaded rod, slotted rod, or flexible wire or ribbon of biocompatible material (such as Nylon®, Prolene® or stainless steel, or any other suitable pharmaceutically acceptable metal or metal alloy, or plastic or polymeric material) with a stop attachment at either end to limit the length of the movement. In certain embodiments, the trajectory guide can engage or interface with the regulator mechanism using a rack-and-pinion gear, an angled gear, an infinite screw, a spool and/or other arrangements depending on the configuration.

As described elsewhere herein, exemplary embodiments of the distraction osteogenesis device include one or more implantable force delivery mechanisms. In certain embodiments, the force delivery mechanisms may be one or more springs. Where used herein the term "spring" refers to a spiral spring, a leaf spring, a coiled spring, a clock spring, a mainspring, an Omega-shaped spring, a U-shaped spring, a torsion spring, an extension spring, or any other type of spring that functions in accordance with the apparatus of then present disclosure. In various embodiments, springs that may be used in association with the cranium are commonly fabricated intra-operatively from 1.5 mm stainless steel pins and store 10-14 Joules (J) per spring. The springs can be fabricated from any suitable biocompatible material such as stainless steel, martensitic-surface steel, titanium Nitinol-titanium alloys or other biocompatible metal or plastic, polymeric, or elastic material. The force delivery mechanism may include a "going barrel" mainspring with wind-up system and/or reduction gears. Other force delivery systems may include piston driven hydraulic systems with fluid transfer from implantable reservoir, regulated by inertial regulators or centrifugal regulators, and controlled by a "rack-strike" mechanism, "striking train" mechanism, "rack and snail" mechanism or other intermittent mechanisms for periodic hydraulic activation of the piston.

As described elsewhere herein, exemplary embodiments of the distraction osteogenesis device of the present disclosure comprise two or more bone attachment devices (e.g., "footplates") and anchors (e.g., screws) which couple the bone attachment devices to the bone targeted by the distraction process. In exemplary embodiments, each bone segment is attached to a separate attachment device using threaded screws, pins, hooks or other suitable anchorage mechanisms. The attachment device may also have several interfaces for the force delivery mechanism, such as various springs and pistons. Multiple interfaces for the force delivery system allow for tailoring the force to the required application. The footplates also interface with the trajectory guides.

Exemplary embodiments of the present disclosure comprise a regulator. In one embodiment, the regulator comprises an escapement wheel, lever and balance wheel and balance spring, attached to high-ratio reduction gears. A mainspring (e.g., a spring as describe elsewhere herein) may be used in such configuration. This mechanism is suitable for relatively low torque applications. When higher torque is needed, the regulator comprises a mechanical time-keeping system of gears, balance spring and wheel, and escapement wheel that provides a consistent pace to a timing wheel. At specific intervals regulated by the timing wheel (e.g., every 1, 12 or 24 hours), a separate "striking wheel" mechanism is triggered, that disengages the trajectory guide through a separate escapement mechanism, allowing distraction or separation of the bone segments.

In such situations when the timing mechanism and striking mechanism are decoupled, the timing mechanism is driven by a "going barrel" mainspring whose arbor is wound with each "strike" activation, using gearing engaged with the trajectory guide, thus replenishing energy provided by the external springs. The main distraction forces are provided by one or more external springs. In other configurations, a "rack strike" mechanism, a "striking train" mechanism, "rack and snail" mechanism or other repeating mechanism is used. Other configurations may include other mechanical regulators such as centrifugal regulators and inertial regulators, with weights attached to a central axis by adjustable springs. Once a certain angular speed is reached, the centrifugal forces on the weights push friction pads against a drum, thus regulating speed. The trajectory guide may be rigidly attached to one footplate, and have a sliding interface with the other footplate, such as a slot, notch or infinite screw. The footplate that is not attached to the trajectory guide may attach to the regulator mechanism. In some configurations, the regulator mechanism engages both footplates with a sliding interface, and interfaces with the trajectory guide, typically using an angled gear.

In certain embodiments, the device may utilize a wireless controller and actuator to control the application of distraction forces. For example, an actuator may be activated via a wireless signal to initiate or cease the application of a distraction force supplied by the device. In certain embodiments, the actuator may be a linear actuator that engages and disengages the regulator mechanism based on a wireless signal received from a controller. In specific embodiments, the actuator may engage and disengage the regulator mechanism by extending or retracting a pin or rod into gear, track or teeth in the regulator mechanism.

In certain embodiments of the distraction osteogenesis device, the actuator may be initially engaged with the regulator mechanism to restrict movement of an attachment device that is anchored to a bone segment and movably secured upon a guide (as described elsewhere herein). After implantation, the actuator can be activated by the wireless controller to disengage from the regulator mechanism and allow movement of the attachment device along the guide thus causing application of a distraction force to the bone segment to which the attachment device is anchored. When the desired amount of distraction of the bone has been attained, the actuator can again be activated by the wireless controller to engage the regulator mechanism and restrict further movement of the attachment device.

It is understood that other embodiments may not utilize a wireless controller to and actuator to control the application of distraction forces, and may rely on mechanical control mechanisms as disclosed elsewhere herein. For example, the device may be configured such that regulator mechanism allows application of distraction forces and movement of the attachment device upon implantation, while the guide restricts the movement of the attachment device to the desired amount (e.g., by limiting movement of the attachment device via a stop attachment as previously discussed).

Certain embodiments of the present disclosure may be implemented using a computer communicatively coupled to a network (for example, the Internet), another computer, or in a standalone computer, or as an Internet of Things (IoT) device (i.e., a smart device which may function on [i.e., as part of] the Internet of Things). As is known to those skilled in the art, a suitable computer can optionally include a processor or central processing unit ("CPU"), at least one read-only memory ("ROM"), at least one random access memory or volatile memory store ("RAM"), at least one non-volatile memory store, for example flash memory or a hard drive ("HD"), and one or more input/output ("I/O") device(s). The I/O devices can include a keyboard, monitor, LCD screen, input buttons or other actuators, printer, internal sensors related to the physical state, position, activity, history, magnetic field, or other aspects of the device, electronic pointing device (for example, mouse, trackball, stylist, touch pad, etc.), or the like.

ROM, RAM, and HD are computer memories for storing computer-executable instructions executable by the CPU or capable of being complied or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" or is not limited to ROM, RAM, and HD and can include any type of data storage medium that can be read by a processor. For example, a computer-readable medium may refer to a data cartridge, a data backup magnetic tape, a floppy diskette, a flash memory module or drive, an optical data storage drive, a CD-ROM, ROM, RAM, HD, or the like. Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language (e.g., C, Assembler, Perl, Python, Java, PHP, Ruby, Swift, Cobol) can be used to implement the routines, methods or programs of embodiments of the present disclosure, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the embodiments of the present disclosure.

The inventive concepts of the present disclosure having now been generally described, reference is now made to the following examples and embodiments, which are included merely for purposes of illustration of certain aspects and embodiments of the inventive concepts of the present disclosure and are not intended to be limitations of the disclosure in any way whatsoever. Those skilled in the art will promptly recognize appropriate variations of the apparatus, compositions, components, procedures and method shown below.

Figure 1:
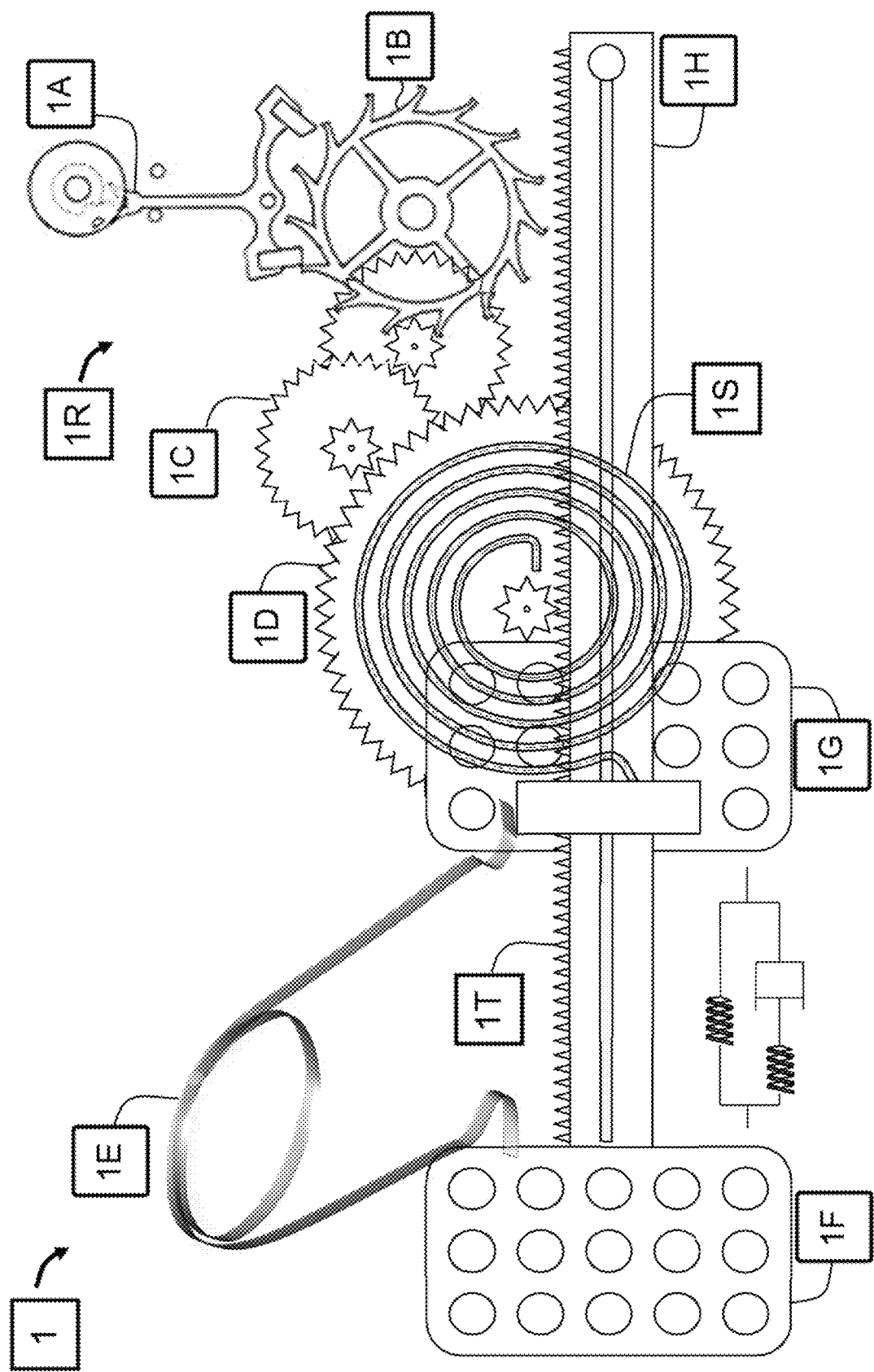
FIG. 1 illustrates a schematic view of an exemplary embodiment of an implantable distraction osteogenesis device 1 according to the present disclosure. In this embodiment, reference numbers and component descriptions are provided as follows:
  1R: Regulator (e.g. comprising balance wheel and balance spring 1A, escapement wheel and lever 1B, and reduction gears 1C)
  1D: Force delivery mechanism (e.g. a spiral spring 1S (mainspring), main wheel, and pinion gear.
  1E: Omega cranial spring engaging with footplates to provide additional tailored force
  1F: Second bone attachment device (e.g. a distal footplate rigidly attached to guide
  1G: First bone attachment device (e.g. a proximal footplate with sliding interface with guide and second bond attachment device to regulator 1R housing.
  1H: Guide (e.g. a trajectory guide with slotted rack, interfacing with main wheel pinion gear (1D), and end-of-trajectory "stop" attachment.

In an exemplary embodiment, a distraction osteogenesis device 1 is shown in FIG. 1, gear (mainspring barrel) 1D engages with three other parts of the device: regulator 1R (comprising parts 1A, 1B and 1C) by geared interface (large wheel portion of gear 1D), rigidly to footplate 1G, and to trajectory guide 1H (with teeth 1T) by geared interface with pinion gear portion of gear 1D. In its interaction with the regulator 1R, mainspring barrel outer gear comprises a wound spiral spring 1S, typically expected to unfurl 5 turns while remaining in the flat portion the force response curve. It is coupled to an outer gear (large wheel), that interfaces with multiple reduction wheels 1C (four in this embodiment), that in turn engage with an escapement wheel B, at a rate controlled by balance wheel and spring 1A, via an anchor lever. The final gearing ratio between the linear gear of the trajectory guide and the escapement wheel is calculated to match the resonance period of the balance spring/balance wheel and a linear motion of trajectory guide H of (in a non-limiting embodiment) about 1 mm per 24 hours. In certain embodiments, the resonance period is controlled by the design parameters of the balance spring (e.g., the wheel weight and the force provided by the spring).

For example, if the balance wheel has a period of one-half second, the escapement wheel may have 20 teeth, and the pinion gear has 8 teeth with 1 mm pitch each, the total reduction ratio is 8*24*60*60*0.5/20=69,120 to 1. In certain embodiments, the total movement allowed by the design is 40 mm, or 5 revolutions of the mainspring axis, over 40 days, although most distraction procedures require less distance. Gear 1D interacts with the trajectory guide 1H, via pinion gear to a flat gear surface fashioned on the lateral surface of the guide in this configuration, with 1 mm pitch teeth. In this embodiment, guide 1H is rigidly assembled to attachment device 1F, and has a sliding slotted interface with attachment device 1G, allowing movement in along a single axis, such that separation of the attachment devices 1F and 1G effects the distraction movement. An end of movement "stop" guard prevents inadvertent over-extension.

Figure 5:
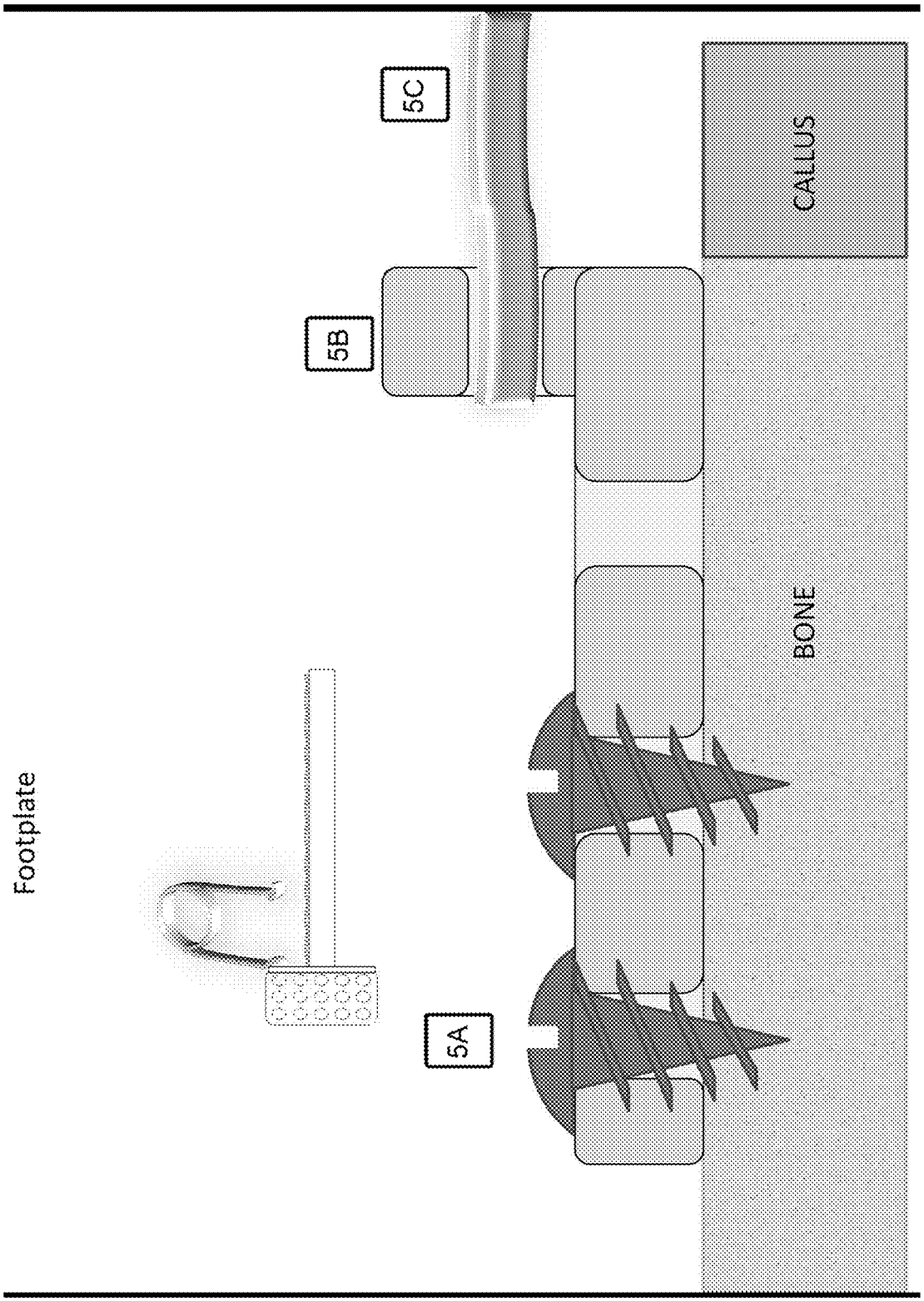
FIG. 5 illustrates a schematic view of an attachment device (e.g. a footplate part), engaging bone and activation spring. The attachment device represented allows engagement of up to six external springs and is shown in top view and cross-section. In this embodiment, reference numbers and component descriptions are provided as follows.

In exemplary embodiments, two bone attachment devices (footplates) 1F and 1G (more can be used if desired) can be secured to bone using common osteosynthesis methods, such as osteosynthesis screws. An osseous gap is formed, for example by the surgeon, in a portion of the bone between the footplates. A healing bone callus will generate within the osseous gap during the distraction process. Attached soft tissues, muscles, tendons, and other tissues react with viscoelastic properties with various force magnitude, depending on site, age, and other properties. Eventually the callus will ossify. Optionally, the force balance can be amplified by using one or more additional springs that can be secured between the two or more footplates. In FIG. 1, an optional additional cranial spring 1E is positioned to be engaged with two footplates. The additional cranial spring may be fashioned by the surgeon during the implantation procedure using stainless steel pins and formed into an omega shape. The one or more additional springs allow tailored force to be applied by using larger diameter pins or multiple springs (see e.g., FIG. 7). The additional cranial spring can be secured to bone attachment devices 1F and 1G using custom slots as illustrated in FIG. 5.

Figure 2:
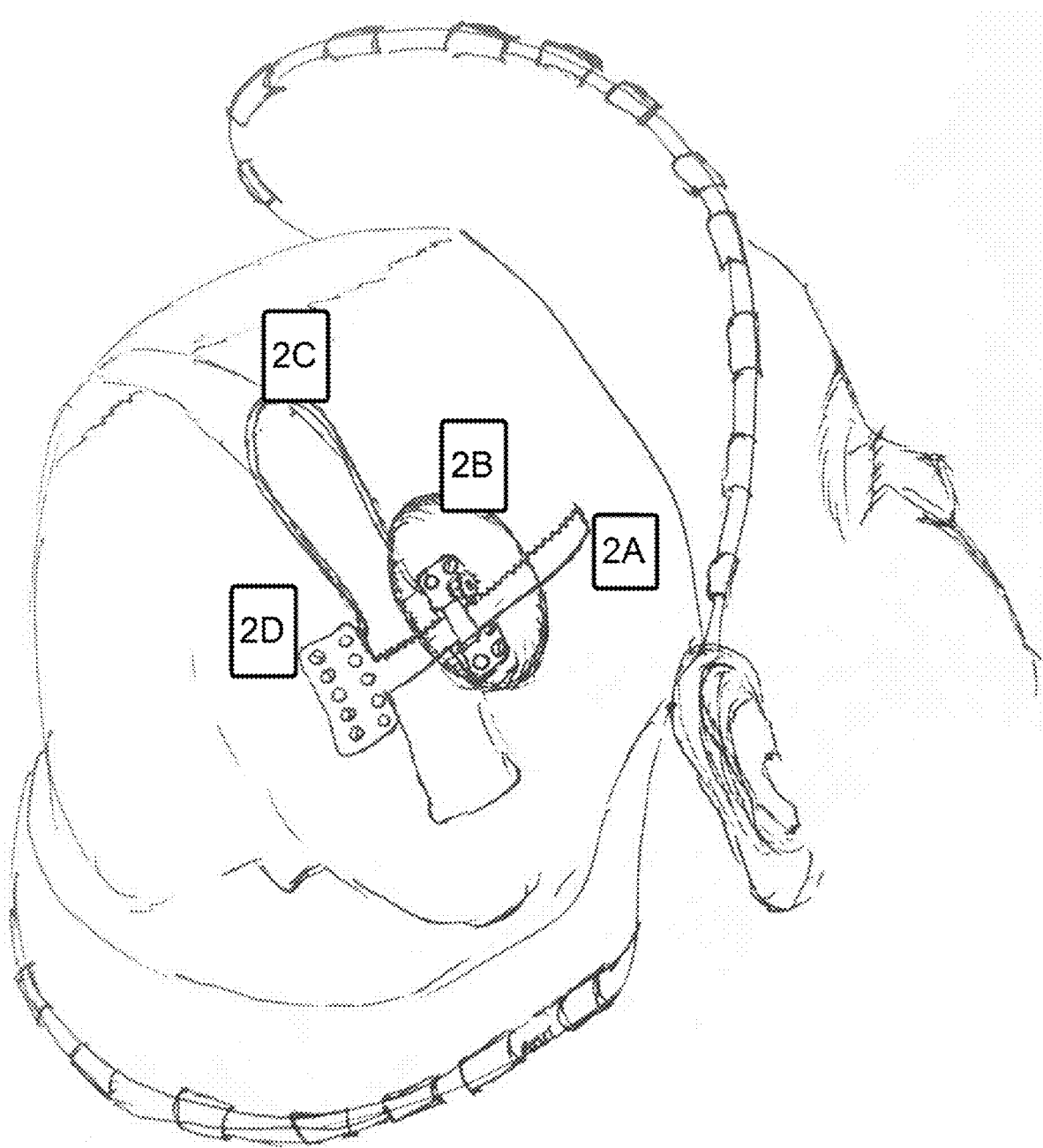
FIG. 2 illustrates a schematic view of an exemplary embodiment of an implantable distraction osteogenesis device according to the present disclosure in a cranial remodeling application. In this embodiment, reference numbers and component descriptions are provided as follows:
  2A: Trajectory guide curved to follow cranial contour.
  2B: Housing for Regulator, spiral spring, and pinion gear, rigidly attached to underlying footplate. The housing sits on top of the footplate, which is seen by transparency.
  2C: Cranial spring providing additional tailored expansion force.
  2D: Distal attachment device (e.g. footplate) rigidly attached to bone with osseous screws, and engaging cranial spring.

In one non-limiting embodiment, an operative procedure may be performed as illustrated in FIG. 2, wherein the skin and subcutaneous tissues are incised and reflected to expose a fused cranial suture which could cause increased pressure on the underlying brain, a condition known as craniosynostosis. In this embodiment, the surgeon makes a bone cut that releases the fused bone, perpendicular to the desired direction of expansion. Typically, more than one cut is made. The surgeon then places the distraction osteogenesis device 1 with its trajectory guide 1H parallel to the desired vector of expansion. The trajectory guide 1H may be contoured in a convex configuration to follow the contour of the cranium, thus guiding the bone movement into a pre-configured trajectory, and minimizing risk of extrusion through soft tissues. The footplates of the distraction osteogenesis device 1 are secured to the edges of the bone with osteosynthesis screws as shown in attachment device 2D. The stiffness and resistance of soft tissues is measured or estimated by the surgeon and additional force delivery devices are added. In this case, a 10 N force is estimated, and a 12 N Cranial Spring is fashioned from 1.5 mm Stainless Steel K-wire into a U-shaped configuration and attached to the footplates of the device. Additional distraction osteogenesis devices 1 may be placed as needed. The regulator mechanism 2B is activated and the skin and soft tissues are closed. No external attachment is required. The distraction process then unfolds over a period of, for example, 1-12 weeks without external intervention. Later, the surgeons may use the same approach to remove the distraction osteogenesis device(s) 1, at which time the osseous gap will have filled with ossified regenerate bone.

Figure 3:
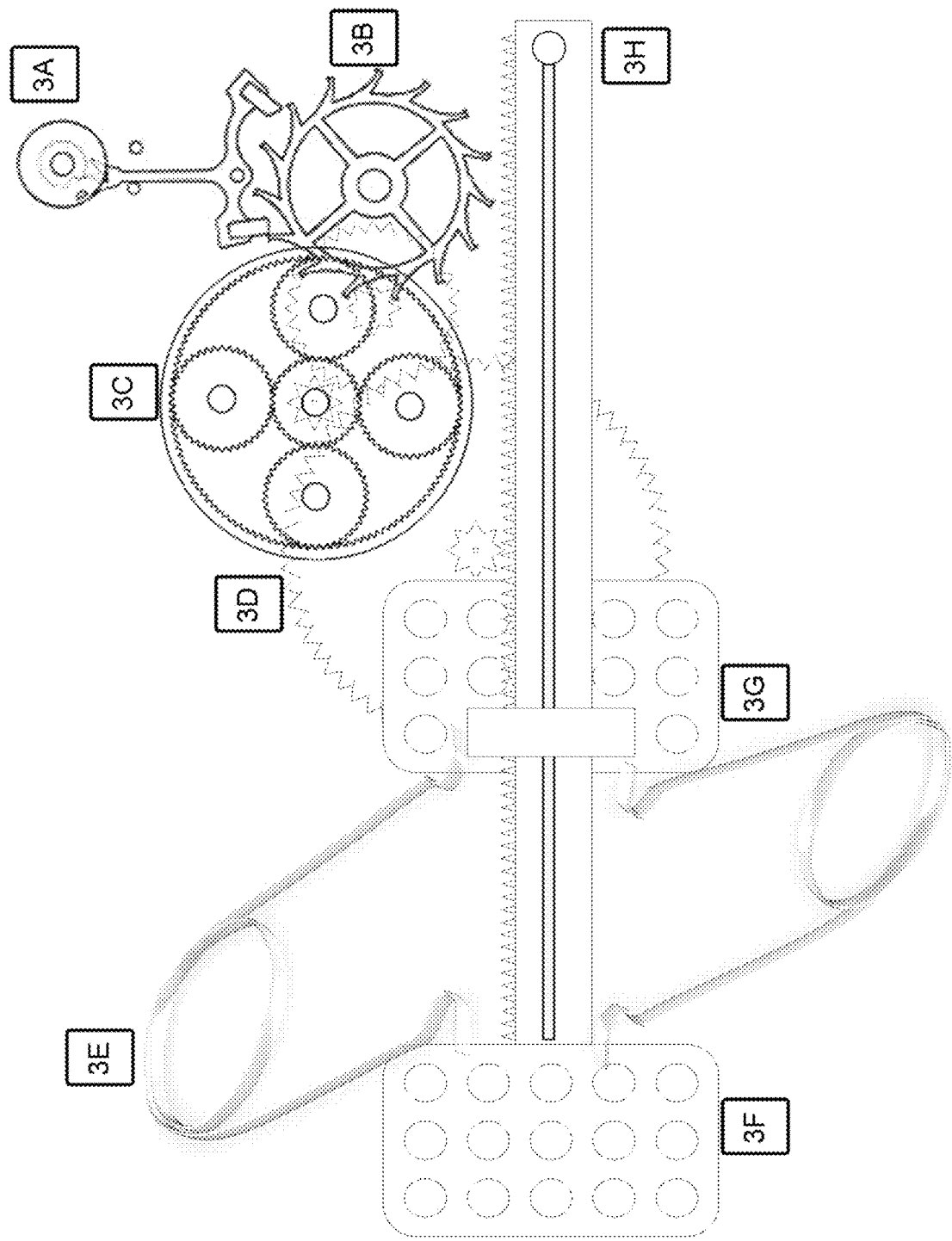
FIG. 3 illustrates a schematic view of an exemplary embodiment of a regulator mechanism without a spiral spring, instead activated by two cranial springs. This embodiment can allow for a smaller profile in certain applications. In this embodiment, reference numbers and component descriptions are provided as follows:
  3A: Balance Wheel and Balance Spring
  3B: Escapement Wheel and Lever
  3C: Planetary gears
  3D: Main Wheel, and pinion gear.
  3E: Omega cranial spring engaging with footplates to provide additional tailored force
  3F: Distal footplate rigidly attached to Trajectory Guide
  3G: Proximal footplate with sliding interface with Trajectory Guide and rigid attachment to Regulator mechanism (3A-3D) housing.
  3H: Trajectory guide with slotted rack, interfacing with main wheel pinion gear (3D), and end-of-trajectory "stop" attachment.
Figure 4:
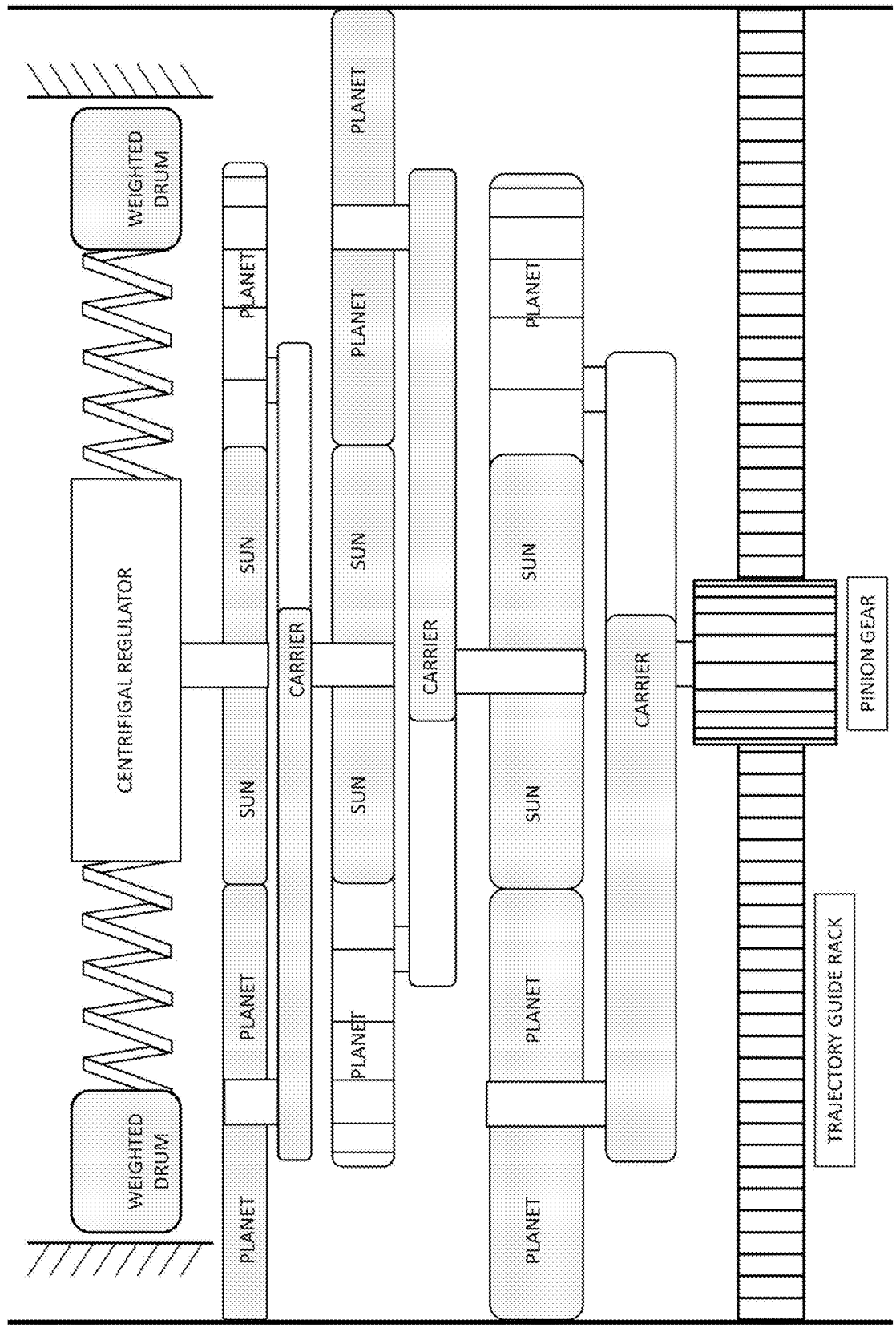
FIG. 4 illustrates a schematic view of a cross section of the regulator housing showing a train of three planetary gear reductions. In this embodiment, a centrifugal regulator is represented with spring-retained weighted pads, which engage a drum surface within the housing. The ring gears are static with the housing and are not represented.

In other embodiments when soft tissue constraints require the contour of the distraction osteogenesis device to be minimized, the force delivery mechanism (mainspring barrel) may be omitted from the regulator mechanism housing (FIGS. 3 and 7). Instead, one or more springs may be applied directly to the two or more footplates (as described above). In other embodiments wherein the pace of distraction may need to be adjustable over a wider range, a centrifugal regulator may replace the balance wheel escapement mechanism. Distraction forces and power to the device may be provided by external springs. Such a device is illustrated in cross section in FIG. 4. In such embodiment, the pinion gear interacts directly with a planetary gear train multiplier that greatly magnifies the angular speed while reducing the torque on the components down the train. Each gear level may offer 10× multiplication and a loss of 3% of energy. The final gear attaches to a centrifugal regulator, which comprises weights retained radially by springs. As the angular speed of the regulator increases, these weights displace away from the central axis, and engage a friction lip further away from the axis of rotation, thus producing more resistance to movement. By adjusting the tension on the radial springs and the height of the friction drum, a precise adjustment of speed is possible.

In other embodiments where higher torque is needed than can be tolerated by the gearing of the regulator, it is possible to decouple the timing mechanism using an internal main spring in a "going barrel" configuration (FIG. 6, part 6C), while the actual distraction forces are provided by the external springs, that may be used to periodically re-wind the mainspring. This embodiment is illustrated in FIG. 6. The timing portion of the regulator final wheel interacts with the main pinion as a holding ring-holding plate escapement (part 6I in FIG. 6). The final gear of the timing mechanism provides a continuous motion escape pinion with a period that corresponds to the desired distraction rate (typically 1 mm in 24 hours, or 0.5 mm every 12 hours, or other rate as described elsewhere herein). This allows a gapless escape of the pinion, now acting as a "scape wheel," under the continuous torque provided by the external springs through the linear gear rack of the trajectory guide. An additional multiplication gearing mechanism is attached to the pinion gear through gear 6K and ratcheted arc-gear 6L to a ratcheted gear M that provides periodic winding of the arbor of main spring 6C. This allows uninterrupted function of the timing mechanism as long as sufficient force is provided by external springs 6E.

In other applications where it is desirable to place the larger housing of the regulator body away from the trajectory guide, an alternate embodiment of the mechanism is shown in FIG. 8. In such embodiment, the distraction distance and pace are regulated by unspooling of a flexible wire attached to the proximal footplate, while the trajectory of the distraction movement is guided by a slotted flat guide.

While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed apparatus and methods.

What is claimed:

1. An implantable distraction osteogenesis device comprising:
   a guide;
   a first bone attachment device slidably engaged with the guide;
   a force delivery mechanism coupled to the first bone attachment device and operably engaged with the guide;
   a regulator operably engaged with the force delivery mechanism, wherein the regulator comprises a centrifugal regulator; and
   a second bone attachment device rigidly fixed to the guide, wherein:
      the force delivery mechanism is configured to exert a force to move the first bone attachment device along the guide at a predetermined rate; and
      the regulator is configured to control the force delivered to the first bone attachment device by the force delivery mechanism thereby controlling movement of the first bone attachment device along the guide without percutaneous intervention, and wherein the distraction osteogenesis device is totally subcutaneously implantable and is absent a percutaneous attachment for externally manipulating an internal portion of the device.

2. The implantable distraction osteogenesis device of claim 1, wherein the predetermined rate is in a range of 0.1 millimeters (mm) to 2.0 mm per 24 hours.

3. The implantable distraction osteogenesis device of claim 1, wherein the guide is configured to move the first bone attachment device in a linear path.

4. The implantable distraction osteogenesis device of claim 1, wherein the guide is configured to move the first bone attachment device in a pre-defined three-dimensional path.

5. The implantable distraction osteogenesis device of claim 1, wherein:
   the guide has a maximum dimension in a range of about 1 to 5 centimeters (cm); and
   the regulator has a maximum dimension in a range of about 1 to 4 cm.

6. The implantable distraction osteogenesis device of claim 1, wherein the force delivery mechanism is configured to generate a force in a range of about 40 N to about 70 N.

7. The implantable distraction osteogenesis device of claim 1, wherein the guide engages the regulator via at least one of a rack-and-pinion gear, an angled gear, an infinite screw, and a spool.

8. An implantable distraction osteogenesis device comprising:
   a guide;
   a first bone attachment device slidably engaged with the guide;
   a force delivery mechanism coupled to the first bone attachment device and operably engaged with the guide;
   a regulator operably engaged with the force delivery mechanism; and
   a second bone attachment device rigidly fixed to the guide, wherein:
      the force delivery mechanism is configured to exert a force to move the first bone attachment device along the guide at a predetermined rate;

the regulator is configured to control the force delivered to the first bone attachment device by the force delivery mechanism thereby controlling movement of the first bone attachment device along the guide without percutaneous intervention, and wherein the distraction osteogenesis device is totally subcutaneously implantable and is absent a percutaneous attachment for externally manipulating an internal portion of the device; and the force delivery mechanism comprises a spring.

9. The implantable distraction osteogenesis device of claim 8, wherein the spring is selected from the group consisting of a spiral spring, a leaf spring, a coiled spring, a clock spring, a mainspring, an Omega-shaped spring, a U-shaped spring, a torsion spring, and an extension spring.

10. An implantable distraction osteogenesis device comprising:
   a guide;
   a first bone attachment device slidably engaged with the guide;
   a force delivery mechanism coupled to the first bone attachment device and operably engaged with the guide;
   a regulator operably engaged with the force delivery mechanism; and
   a second bone attachment device rigidly fixed to the guide, wherein:
      the force delivery mechanism is configured to exert a force to move the first bone attachment device along the guide at a predetermined rate; and
      the regulator is configured to control the force delivered to the first bone attachment device by the force delivery mechanism thereby controlling movement of the first bone attachment device along the guide without percutaneous intervention, and wherein the distraction osteogenesis device is totally subcutaneously implantable and is absent a percutaneous attachment for externally manipulating an internal portion of the device; and
   wherein the regulator further comprises:
      a balance wheel and balance spring;
      an escapement wheel and lever;
      one or more reduction gears;
      a spiral spring;
      a primary gear; and
      a pinion gear.

11. The implantable distraction osteogenesis device of claim 10, wherein:
   the guide comprises a plurality of teeth; and
   the pinion gear of the regulator engages the plurality of teeth.

12. An implantable distraction osteogenesis device comprising:
   a guide;
   a first bone attachment device slidably engaged with the guide;
   a force delivery mechanism coupled to the first bone attachment device and operably engaged with the guide;
   a regulator operably engaged with the force delivery mechanism; and
   a second bone attachment device rigidly fixed to the guide, wherein:
      the force delivery mechanism is configured to exert a force to move the first bone attachment device along the guide at a predetermined rate;
      the regulator is configured to control the force delivered to the first bone attachment device by the force delivery mechanism thereby controlling movement of the first bone attachment device along the guide without percutaneous intervention, and wherein the distraction osteogenesis device is totally subcutaneously implantable and is absent a percutaneous attachment for externally manipulating an internal portion of the device; and
      the regulator is configured to control movement of the first bone attachment device along the guide without percutaneous intervention for a period in a range of 1 to 90 days.

13. A method of causing distraction osteogenesis in a bone of a subject in need of such therapy, the method comprising:
   (a) providing an implantable distraction osteogenesis device comprising:
      a guide;
      a first bone attachment device slidably engaged with the guide;
      a force delivery mechanism coupled to the first bone attachment device and operably engaged with the guide;
      a regulator operably engaged with the force delivery mechanism wherein the regulator comprises a centrifugal regulator; and
      a second bone attachment device rigidly fixed to the guide, wherein:
         the force delivery mechanism is configured to exert a force to move the first bone attachment device along the guide at a predetermined rate; and
         the regulator is configured to control the force delivered to the first bone attachment device by the force delivery mechanism thereby controlling movement of the first bone attachment device along the guide without percutaneous intervention;
   (b) securing the first bone attachment device and the second bone attachment device to the bone of the subject, wherein the distraction osteogenesis device is completely subcutaneously implanted and is absent a percutaneous attachment for externally manipulating an internal portion of the device; and
   (c) actuating the distraction osteogenesis device thereby causing a distraction force to be applied between the first bone attachment device and the second bone attachment device, wherein the distraction osteogenesis device operates without percutaneous intervention after actuation.

14. The method of claim 13, wherein the distraction osteogenesis device is operated for a period of time sufficient to enable a predetermined amount of distraction osteogenesis in the bone.

15. The method of claim 13, wherein the implantable distraction osteogenesis device further comprises a spring that engages the first bone attachment device and the second bone attachment device to provide an expansion force between the first bone attachment device and the second bone attachment device.

16. The method of claim 13, wherein the bone is selected from the group consisting of a skull, a cranium, a mandible, a facial bone, a femur, a tibia, a fibula, a humerus, an ulna, a radius a phalange, a metacarpal, and a vertebra.

17. The method of claim 13, wherein the distraction osteogenesis device is actuated by a wireless controller.

* * * * *